(12) United States Patent
Khayyat (10) Patent No.: US 10,584,106 B1
(45) Date of Patent: Mar. 10, 2020

(54) ANTIFUNGAL COMPOUNDS DERIVED FROM LAVENDER OIL

(71) Applicant: King Abdulaziz University, Jeddah (SA)

(72) Inventor: Suzan Khayyat, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 16/122,271

(22) Filed: Sep. 5, 2018

(51) Int. Cl.
C07D 301/12 (2006.01)
C07D 303/16 (2006.01)
A61P 31/10 (2006.01)
C07C 409/04 (2006.01)
C07C 407/00 (2006.01)

(52) U.S. Cl.
CPC ............ *C07D 301/12* (2013.01); *A61P 31/10* (2018.01); *C07C 407/00* (2013.01); *C07C 409/04* (2013.01); *C07D 303/16* (2013.01)

(58) Field of Classification Search
None
See application file for complete search history.

(56) References Cited

FOREIGN PATENT DOCUMENTS

| CN | 103880653 A | 6/2014 |
|---|---|---|
| WO | 2013-059364 A2 | 4/2013 |

OTHER PUBLICATIONS

Wasylashuk et al. Evaluation of hydroperoxides in common pharmaceutical excipients. Journal of Pharmaceutical Sciences, vol. 96, No. 1 Jan. 2007.*
Santos et al. Catalytic homogeneous oxidation of monoterpenes and cyclooctene with hydrogen peroxide in the presence of sandwich-type tungstophosphates. Journal of Molecular Catalysis A: Chemical 426, 2017, 593-599.*
Rudback, et al. ; Determination of allergenic hydroperoxides in essential oils using gas chromatography with electron ionization mass spectrometry ; Journal of Separation Science, vol. 37, Issue 8 ; Jan. 30, 2014 ; Abstract.
Rudback, et al. ; A sensitive method for determination of allergenic fragrance terpene hydroperoxides using liquid chromatography coupled with tandem mass spectrometry ; Journal of Separation Science, vol. 36, Issue 8 ; Feb. 13, 2013 ; Abstract.
Skold, et al. ; Autoxidation of linalyl acetate, the main component of lavender oil, creates potent contact allergens ; Contact Dermatitis, vol. 58, Issue 1 ; Nov. 27, 2007 ; Abstract.
Ngnokam, et al. ; 4,5-Epoxide-1,6-Dimethyl-1-Vinylhexyl p-Coumarate: A Novel Monoterpene Derivative From Cleistopholis Patens ; Bull. Chem. Soc. Ethiop. 2003, 17(2), 177-180 ; 4 pages.
Mischitz, et al. ; Chemo-enzymatic Synthesis of (2R,5S)- and (2R,5R)-5-(1-Hydroxy-1-methylethyl)-2-methyl-2-vinyltetrahydrofuran ('Linalool Oxide'): Preparative Application of a Highly Selective Bacterial Epoxide Hydrolase ; Thieme E-Journals—Synlett ; Dec. 31, 2000 ; Abstract.

(Continued)

*Primary Examiner* — Anna Pagonakis
(74) *Attorney, Agent, or Firm* — Oblon, McClelland, Maier & Neustadt, L.L.P.

(57) ABSTRACT

Epoxides and hydroperoxide compounds having antifungal activities derived from the oxidation linalyl acetate, a major component of lavender oil, are disclosed. Also, disclosed are pharmaceutical composition and methods of treating and protecting a subject from fungal infection.

18 Claims, 4 Drawing Sheets

1

2

(56) References Cited

OTHER PUBLICATIONS

Zdero, et al. ; Glaucolides, fulvenoguaianolides and other sesquiterpene lactones from Pentzia species ; ScienceDirect ; Phytochemistry, vol. 29, Issue 1 , 1990, pp. 189-194 ; Abstract.
Zdero, et al. ; Sesquiterpene lactones and other constituents from Eriocephalus species ; ScienceDirect ; Phytochemistry, vol. 26, Issue 10, 1987, pp. 2763-2775 ; Abstract.
Zdero, et al. ; Further 5-methyl coumarins and other constituents from the subtribe mutisiinae ; ScienceDirect ; Phytochemistry, vol. 25, Issue 2, Jan. 22, 1986, pp. 509-516 ; Abstract.
Tabushi, et al. ; Stereospecific, regioselective, and catalytic monoepoxidation of polyolefins by the use of a P-450 model, dihydrogen-dioxygen—TPP.cntdot.Mn-colloidal platinum ; Journal of the American Chemical Society, 106 (22) pp. 6871-6872 ; Oct. 1984 ; 1 page.
Mookherjee, et al. ; Isolation, identification, and biogenesis of bifunctional compounds in lavandin oil ; Journal of Agricultural and Food Chemistry ; 21 (2), pp. 298-302, Mar. 1973 ; 1 page.

\* cited by examiner

Scheme 1

Figure 3

Scheme 2

Figure 4

Scheme 3

ANTIFUNGAL COMPOUNDS DERIVED FROM LAVENDER OIL

BACKGROUND OF THE INVENTION

Field of the Disclosure

The present invention relates to oxidation products derived from lavender oil having antifungal activity.

Description of Related Art

The use of medicinal plants and folk medicines are wide spread in the world. In folk medicines and aroma therapy, essential oils and fragrance compounds are being used as therapeutic agents for relieving pain, anxiety reduction, and energy enhancement [Kako et al. "Effects of direct exposure of green odor components on dopamine release from rat brain striatal slices and PC12 cells" Brain Res. Bull, 75 (2008), pp. 706-712; Kiecolt-Glaser et al. "Olfactory influences on mood and autonomic, endocrine, and immune function" Psychoneuroendocrinology, 33 (9) (2008), p. 1303; Emmanuel et al. "Essential oil constituents, anticancer and antimicrobial activity of *Ficus mucoso* and *Casuarina equisetifolia* leaves" Am. J. Essent. Oils Nat. Prod., 4 (2016), pp. 01-06]. The highly volatile acyclic monoterpenes are major components of essential oils and fragrance and are used in both the flavor and fragrance industries [King et al. "Biotransformation of hop aroma terpenoids by ale and lager yeasts" FEMS Yeast Res., 3 (2013), pp. 53-62; and Elsharif et al. "Structure-odor relationships of linalool, linalyl acetate and their corresponding oxygenated derivatives" Front. Chem., 3 (2015), pp. 57-61].

Lavender is a common and popular aromatic Mediterranean herb belongs to Lamiaceae family growing almost all over the world. It is marketed as the fresh or dried plant [Ruriko et al. (2006) "Linalyl acetate as a major ingredient of lavender essential oil relaxes the rabbit vascular smooth muscle through dephosphorylation of myosin light chain" J. Cardiovasc. Pharmacol., 48 (1) pp. 850-856]. Also, it is considered as a treatment of pain and tremor [Gorji, and Ghadiri (2002) "History of headache in medieval Persian medicine" Lancet Neurol., 1 (8) pp. 510-515; Gorji, A. "Pharmacological treatment of headache using traditional Persian medicine" Trends Pharmacol. Sci., 24 (7) (2003), pp. 331-334; and Vakili, and Gorji (2006) "Psychiatry and psychology in medieval Persia" J. Clin. Psychiatry, 67 (12) pp. 1862-1869].

Figure 1:
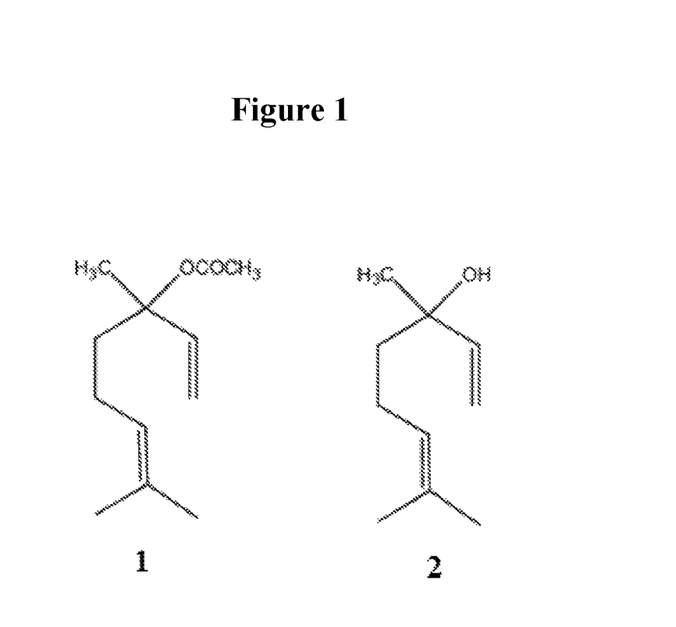
FIG. 1 shows the chemical structure of compounds 1 and 2.

Linalyl acetate 1 and linalool 2 (see FIG. 1) are the most abundant acyclic monoterpene substances which represent about 70% of the terpenoids of floral scents [Cavanagh and Wilkinson (2002) Biological activities of lavender essential oil Phytother. Res., 16 (4) (2002), pp. 301-308; Stashenko and Martinez "Sampling flower scent for chromatographic analysis" J. Sep. Sci., 31 (2008), pp. 2022-2031; Skold et al. "Autoxidation of linalyl acetate, the main component of lavender oil, creates potent contact allergens" Contact Dermatitis, 58 (2008), pp. 9-14; Woronuk et al. "Biosynthesis and therapeutic properties of lavandula essential oil constituents" Planta Med., 77 (1) (2011), pp. 7-15]. They are found in essential oils of over 200 plant species, belonging to different families (Cavanagh and Wilkinson, 2002). Linalyl acetate 1 and linalool 2 are the main components of lavender oil. The odor of linalyl acetate is described as floral, sweet and citric, as well as minty and slightly caraway-like [d'Acampora et al. Odour fingerprint acquisition by means of comprehensive two-dimensional gas chromatography-olfactometry and comprehensive two-dimensional gas chromatography/mass spectrometry J. Chromatogr. A, 1141 (2007), pp. 279-286]. Linalyl acetate was reported to have anti-inflammatory activity [Peana et al. "Anti-inflammatory activity of linalool and linalyl acetate constituents of essential oils" Phytomedicine 9 (2002), pp. 721-726].

Plant monoterpenes are amenable to air oxidation which is enhanced by exposure to heat, light, or by chemical catalysts. Photo-oxidation monoterpenes is believed to proceed by a mechanism involves reactive singlet oxygen leading to the formation of hydroperoxides in the presence of oxygen, light, and photosensitizers [Elgendy and Khayyat "Oxidation studies on some natural monoterpenes: citral, pulegone and camphene Russ. J. Org. Chem., 44 (6) (2008a), pp. 814-822; and "Oxidation reactions of some natural volatile aromatic compounds: anethole eugenol" Russ. J. Org. Chem., 44 (6) (2008b), pp. 823-829]. Hydroperoxides may give rise to secondary oxidation products having multiple chemical functional groups such as hydroxyl, carbonyl, and epoxide [Elgendy and Khayyat, 2008a, 2008b]. Also, unsaturated terpenes are capable of trapping activated oxygen species in vivo to give intermediate epoxides which are known to alkylate DNA, proteins, and other biomolecules [Méou et al. "Oxygen transfer mechanism in the Mn-salen catalysed epoxidation of olefins" J. Mol. Catal. A Chem., 138 (2) (1999), pp. 221-226; Richter et al. "Clerocidin alkylates DNA through its epoxide function: evidence for a fine tuned mechanism of action" Nucl. Acids Res., 3 (2003), pp. 5149-5156; and Geraghty, N (2005) Photochemistry. In: Dunkin (Ed.), London: Royal Soc. Chem. 27. pp. 35-116]. In addition, monoterpenes undergo epoxidation reaction by hydrogen peroxide to produce terpene epoxide [Yarovaya et al. "Acid-catalyzed reactions of camphene and α-fenchene epoxide" Russ. J. Org. Chem., 38 (2002), pp. 810-822; and Yarovaya et al. "Synthesis of heterocyclic compounds in acid-catalyzed reactions of citral epoxides Mendeleev Commun., 27 (2003), pp. 1-2]. The epoxidation reaction by hydrogen peroxide proceeds via thermal or photochemical reactions pathway [Saddiq and Khayyat "Chemical and antimicrobial studies of monoterpene: citral Pest" Biochem. Physiol., 98 (2010), pp. 89-91].

Accordingly, it is an object of the present disclosure to provide antifungal compounds derived from the thermal and photochemical oxidation of linalyl acetate. The compounds can be formulated into a pharmaceutical composition for use in a method of treatment of fungal infection.

SUMMARY

According to a first aspect of the invention, the current disclosure relates antifungal epoxides and hydroperoxides.

In a preferred embodiment, an epoxide compound having a structure selected from the group consisting of Formula A and B, Formula A -continued

Formula B wherein $R_4$, $R_6$, $R_7$, $R_8$, and $R_9$ are independently hydrogen, optionally substituted alkyl, optionally substituted cycloalkyl, optionally substituted aryl, $R_{13}CO$, $COOR_{14}$, $OR_{15}$, and $NR_{16}R_{17}$, and $R_1$, $R_2$, $R_3$, $R_5$, $R_{10}$, $R_{11}$, $R_{12}$, $R_{13}$, $R_{14}$, $R_{15}$, $R_{16}$, and $R_{17}$ are independently hydrogen, optionally substituted alkyl, optionally substituted cycloalkyl, optionally substituted aryl with the proviso that a compound of formula B has at least one of $R_1$, $R_2$, $R_3$, $R_4$, $R_5$, $R_6$, $R_7$, $R_8$, $R_9$ $R_{10}$, and $R_{11}$ is not a hydrogen.

In a more preferred embodiment, the compound has the structure formula of A or B and $R_4$, $R_5$, $R_{11}$, and $R_{12}$ are optionally substituted alkyl, and $R_1$, $R_2$, $R_3$, $R_6$, $R_7$, $R_8$, $R_9$, and $R_{10}$ are hydrogens.

In the most preferred embodiment, the epoxide compound has antifungal activity.

In the most preferred embodiment, the compound has the structure of compound 4:

Compound 4

In another preferred embodiment, a hydroperoxide compound having the structure Formula C,

Formula C wherein $R_4$, $R_6$, $R_7$, $R_8$, and $R_9$ are independently hydrogen, optionally substituted alkyl, optionally substituted cycloalkyl, optionally substituted aryl, $R_{14}CO$, $COOR_{15}$, $OR_{16}$, and $NR_{17}R_{18}$, and $R_1$, $R_2$, $R_3$, $R_5$, $R_{10}$, $R_{11}$, $R_{12}$, $R_{13}$, $R_{14}$, $R_{15}$, $R_{16}$, $R_{17}$, and $R_{18}$ are independently hydrogen, optionally substituted alkyl, optionally substituted cycloalkyl, optionally substituted aryl with the proviso that at least one of $R_1$, $R_2$, $R_3$, $R_4$, $R_5$, $R_6$, $R_7$, $R_8$, $R_9$ $R_{10}$, $R_{11}$, $R_{12}$, and $R_{13}$ is not a hydrogen.

In a more preferred embodiment, the hydroperoxide compound has antifungal activity.

In another preferred embodiment, the compound has the structure formula of C, wherein $R_4$, $R_5$, and $R_{11}$ are optionally substituted alkyl, and $R_1$, $R_2$, $R_3$, $R_6$, $R_7$, $R_8$, $R_9$, $R_{10}$, $R_{12}$, and $R_{13}$ are independently hydrogen, and optionally substituted alkyl with the proviso that at least one of $R_1$, $R_2$, $R_3$, $R_4$, $R_5$, $R_6$, $R_7$, $R_8$, $R_9$, $R_{10}$, $R_{12}$, and $R_{13}$ is not a hydrogen.

In another preferred embodiment, a hydroperoxide compound having the structure Formula D,

Formula D wherein $R_4$, $R_6$, $R_7$, $R_{10}$, and $R_{11}$ are independently hydrogen, optionally substituted alkyl, optionally substituted cycloalkyl, optionally substituted aryl, $R_{12}CO$, $COOR_{13}$, $OR_{14}$, and $NR_{15}R_{16}$, and $R_1$, $R_2$, $R_3$, $R_5$, $R_8$, $R_9$, $R_{12}$, $R_{13}$, $R_{14}$, $R_{15}$, and $R_{16}$ are independently hydrogen, optionally substituted alkyl, optionally substituted cycloalkyl, optionally substituted aryl with the proviso that at least one of $R_1$, $R_2$, $R_3$, $R_4$, $R_5$, $R_6$, $R_7$, $R_8$, $R_9$ $R_{10}$, and $R_{11}$ is not a hydrogen.

In a more preferred embodiment, the hydroperoxide compound has the structure formula of D, wherein $R_4$, $R_5$, $R_{10}$, and $R_{11}$ are alkyl, and $R_1$, $R_2$, $R_3$, $R_6$, $R_7$, $R_8$, and $R_9$ are independently hydrogen, optionally substituted alkyl, optionally substituted cycloalkyl, optionally substituted aryl with the proviso that at least one of $R_1$, $R_2$, $R_3$, $R_4$, $R_5$, $R_6$, $R_7$, $R_8$, $R_9$, $R_{10}$, and $R_{11}$ is not a hydrogen.

In a more preferred embodiment, the hydroperoxide compound has antifungal activity.

A second aspect of the disclosure is directed to a photochemical method of making the compound of antifungal compound comprising irradiating a solution of formula E, Formula E in a solvent in the presence of hydrogen peroxide or oxygen, wherein $R_4$, $R_6$, $R_7$, $R_8$, and $R_9$ are independently hydrogen, optionally substituted alkyl, optionally substituted cycloalkyl, optionally substituted aryl, $R_{13}CO$, $COOR_{14}$, $OR_{15}$, and $NR_{16}R_{17}$, and $R_1$, $R_2$, $R_3$, $R_5$, $R_{10}$, $R_{11}$, $R_{12}$, $R_{13}$, $R_{14}$, $R_{15}$, $R_{16}$, and $R_{17}$ are independently hydrogen, optionally substituted alkyl, optionally substituted cycloalkyl, optionally substituted aryl.

In a preferred embodiment, the method utilizes a compound of formula E, wherein, $R_6$, $R_7$, $R_8$, $R_9$, and $R_{10}$ are independently hydrogen, and $R_4$, $R_5$, $R_{11}$, and $R_{12}$ are optionally substituted alkyl, optionally substituted cycloalkyl, optionally substituted aryl.

In another preferred embodiment of the method, hydrogen peroxide is present.

In another preferred embodiment of the method, oxygen is present and the solution further comprising a photosensitizer.

In a more preferred embodiment of the method, the photosensitizer is selected from the group consisting of Rose Bengal, methylene blue hematoporphyrin, and tetraphenylprophyrin.

A third aspect of the invention is directed to a pharmaceutical composition comprising one or more antifungal epoxides and/or hydroperoxides disclosed herein.

In a preferred embodiment, the pharmaceutical composition comprises at least one compound of formula A and/or B.

In a more preferred embodiment, the pharmaceutical composition further comprises carriers and/or excipients In the most preferred embodiment of the invention, the composition comprises compound 4.

In another preferred embodiment, the pharmaceutical composition comprises one or more compound of formula C.

In another preferred embodiment, the pharmaceutical composition comprises one or more compound of formula D.

A fourth aspect of the invention is directed to a method of treating or protecting a subject from fungal infection.

In a preferred embodiment, the method comprises administering to a subject effective amount of a pharmaceutical composition comprising one or more epoxide compound having the formula A and/or B.

In a preferred embodiment, the subject is a mammal.

In a more preferred embodiment, the subject is human.

In another preferred embodiment, the method comprises administering to a subject effective amount of a pharmaceutical comprising one or more hydroperoxide compound having formula C.

In another preferred embodiment, the method comprises administering to a subject effective amount of a pharmaceutical comprising one or more hydroperoxide compound having formula D.

In a more preferred embodiment, the method comprises administering to a subject effective amount of a pharmaceutical comprising one or more compounds selected from the group consisting of compounds 1, 3, 4, 5, and 6.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Embodiments of the present disclosure will now be described more fully hereinafter with reference to the accompanying drawings, in which some, but not all embodiments of the disclosure are shown. The present disclosure will be better understood with reference to the following definitions.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Also, the use of "or" means "and/or" unless stated otherwise. Similarly, "comprise," "comprises," "comprising" "include," "includes," and "including" are interchangeable and not intended to be limiting.

As used herein, the terms "compound" is intended to refer to a chemical entity, whether in a solid, liquid or gaseous phase, and whether in a crude mixture or purified and isolated.

As used herein a "polymer" or "polymeric resin" refers to a large molecule or macromolecule, of many repeating subunits and/or substances composed of macromolecules. As used herein a "monomer" refers to a molecule or compound that may bind chemically to other molecules to form a polymer. As used herein the term "repeat unit" or "repeating unit" refers to a part of the polymer or resin whose repetition would produce the complete polymer chain (excluding the end groups) by linking the repeating units together successively along the chain. The method by which monomers combine end to end to form a polymer is referred to herein as "polymerization" or "polycondensation", monomers are molecules which can undergo polymerization, thereby contributing constitutional repeating units to the structures of a macromolecule or polymer. As used herein "resin" or "polymeric resin" refers to a solid or highly viscous substance or polymeric macromolecule containing polymers, preferably with reactive groups. As used herein a "copolymer" refers to a polymer derived from more than one species of monomer and are obtained by "copolymerization" of more than one species of monomer. Copolymers obtained by copolymerization of two monomer species may be termed bipolymers, those obtained from three monomers may be termed terpolymers and those obtained from four monomers may be termed quarterpolymers, etc. As used herein, "cross-linking", "cross-linked" or a "cross-link" refers to polymers and resins containing branches that connect polymer chains via bonds that link one polymer chain to another.

The cross-link may be an atom, a group of atoms, or a number of branch points connected by bonds, groups of atoms, or polymer chains. In the majority of cases, a cross-link is a covalent structure or covalent bond but the term may also describe sites of weaker chemical interactions, portion crystallites, and even physical interactions and entanglements. The cross-linking can alter the physical and mechanical properties of the polymer. Cross-linking may be formed by chemical reactions that are initiated by heat, pressure, change in pH, and/or radiation, with or without the presence of a cross-linking agent and/or catalyst. In certain embodiments, at least one diaminoalkane a cross-linking agent for the cross-linked polymeric resin described herein.

As used herein, the term "salt" refers to derivatives of the disclosed compounds, monomers or polymers wherein the parent compound is modified by making acid or base salts thereof. Exemplary salts include, but are not limited to, mineral or organic acid salts of basic groups such as amines, and alkali or organic salts of acidic groups such as carboxylic acids. The salts of the present disclosure can be synthesized from the parent compound that contains a basic or acidic moiety by conventional chemical methods. Generally such salts can be prepared by reacting the free acid or base forms of these compounds with a stoichiometric amount of the appropriate base or acid in water or in an organic solvent, or in a mixture of the two; generally non-aqueous media like ether, ethyl acetate, ethanol, isopropanol, or acetonitrile are preferred.

As used herein, the term "about" refers to an approximate number within 20% of a stated value, preferably within 15% of a stated value, more preferably within 10% of a stated value, and most preferably within 5% of a stated value. For example, if a stated value is about 8.0, the value may vary in the range of 8±1.6, 1.0, ±0.8, ±0.5, ±0.4, ±0.3, ±0.2, or ±0.1.

As used herein, the term "solvate" refers to a physical association of a compound, monomer or polymer of this disclosure with one or more solvent molecules, whether organic or inorganic. This physical association includes hydrogen bonding. In certain instances, the solvate will be capable of isolation, for example when one or more solvent molecules are incorporated in the crystal lattice of a crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvates include, but are not limited to, hydrates, ethanolates, methanolates, isopropanolates and mixtures thereof. Methods of solvation are generally known to those of ordinary skill in the art.

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, non-enantiomeric optical isomers. Diastereomers seldom have the same physical properties. In terms of the present disclosure, stereoisomers may refer to enantiomers, diastereomers or both.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopes of oxygen include $^{16}O$, $^{17}O$ and $^{18}O$. Isotopically labeled compounds of the invention can generally be prepared by conventional techniques known to those skilled in the art or by processes and methods analogous to those described herein, using an appropriate isotopically labeled reagent in place of the non-labeled reagent otherwise employed.

As used herein, the term "substituted" refers to at least one hydrogen atom that is replaced with a non-hydrogen group, provided that normal valences are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylamino, thiol, alkylation, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like.

As used herein, the term "alkyl" unless otherwise specified refers to both branched and straight chain saturated aliphatic primary, secondary, and/or tertiary hydrocarbons of typically $C_1$ to $C_{10}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. As used herein, the term optionally includes substituted alkyl groups. Exemplary moieties with which the alkyl group can be substituted may be selected from the group including, but not limited to, hydroxyl, amino, alkylamino, arylamino, alkoxy, aryloxy, nitro, cyano, sulfonic acid, sulfate, phosphonic acid, phosphate, or phosphonate or mixtures thereof. The substituted moiety may be either protected or unprotected as necessary, and as known to those skilled in the art.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

As used herein, the term "aryl" unless otherwise specified refers to functional groups or substituents derived from an aromatic ring including, but not limited to, phenyl, biphenyl, naphthyl, thienyl, and indolyl. As used herein, the term optionally includes both substituted and unsubstituted moieties. Exemplary moieties with which the aryl group can be substituted may be selected from the group including, but not limited to, hydroxyl, amino, alkylamino, arylamino, alkoxy, aryloxy, nitro, cyano, sulfonic acid, sulfate, phosphonic acid, phosphate or phosphonate or mixtures thereof. The substituted moiety may be either protected or unprotected as necessary, and as known to those skilled in the art.

A first aspect of the invention is directed to antifungal compounds having a structure selected from the group consisting of Formula A, B, C, and D.

Formula A

Formula B

Formula C

Formula D

A preferred embodiment of the invention is an epoxide having formula A or B, wherein $R_4$, $R_6$, $R_7$, $R_8$, and $R_9$ are independently hydrogen, optionally substituted alkyl, optionally substituted cycloalkyl, optionally substituted aryl, $R_{13}CO$, $COOR_{14}$, $OR_{15}$, and $NR_{16}R_{17}$, and $R_1$, $R_2$, $R_3$, $R_5$, $R_{10}$, $R_{11}$, $R_{12}$, $R_{13}$, $R_{14}$, $R_{15}$, $R_{16}$, and $R_{17}$ are independently hydrogen, optionally substituted alkyl, optionally substituted cycloalkyl, optionally substituted aryl with the proviso that at least one of $R_1$, $R_2$, $R_3$, $R_4$, $R_5$, $R_6$, $R_7$, $R_8$, $R_9$, $R_{10}$, and $R_{11}$ in formula B is not a hydrogen. An epoxide of formula A comprises at least two chiral centers at C2 and C3, and thus, has two pairs of enantiomers having the absolute configuration of (S, S), (R, R), (R, S), and (S, R). Similarly, an epoxide of formula B has two chiral centers at C3 and C6, and has two pairs of enantiomers. The epoxide of the invention may be enatiomerically pure or a mixture of two or more of the stereoisomers.

In a more preferred embodiment, the compound has the structure formula of A or B and $R_4$, $R_5$, $R_{11}$, and $R_{12}$ are independently optionally substituted alkyl, optionally substituted cycloalkyl, optionally substituted aryl, and $R_1$, $R_2$, $R_3$, $R_6$, $R_7$, $R_8$, $R_9$, and $R_{10}$ are hydrogens.

Compound 4

In the most preferred embodiment, the compound has the structure of compound 4. In one embodiment, compound 4 is a single stereoisomer having a configuration selected from the group consisting of (S, S), (R, R), (R, S), and (S, R). In some other preferred embodiment, compound 4 is a racemic mixture containing a pair of enantiomers or a mixture of all four stereoisomers.

Another preferred embodiment of the invention is a hydroperoxide having formula C, wherein $R_4$, $R_6$, $R_7$, $R_8$, and $R_9$ are independently hydrogen, optionally substituted alkyl, optionally substituted cycloalkyl, optionally substituted aryl, $R_{14}CO$, $COOR_{15}$, $OR_{16}$, and $NR_{17}R_{18}$, and $R_1$, $R_2$, $R_3$, $R_5$, $R_{10}$, $R_{11}$, $R_{12}$, $R_{13}$, $R_{14}$, $R_{15}$, $R_{16}$, $R_{17}$, and $R_{18}$ are independently hydrogen, optionally substituted alkyl, optionally substituted cycloalkyl, optionally substituted aryl. The hydroperoxide of formula C comprises at least two chiral centers at C3 and C6, and thus, has two pairs of enantiomers having the absolute configuration of (S, S), (R, R), (R, S), and (S, R). The compound may be enatiomerically pure or a mixture of two or more of the stereoisomers.

In a more preferred embodiment, the hydroperoxide compound has the structure formula of C, wherein $R_4$, $R_5$, and $R_{11}$ are independently optionally substituted alkyl, and $R_1$, $R_2$, $R_3$, $R_6$, $R_7$, $R_8$, $R_9$, $R_{10}$, $R_{12}$, and $R_{13}$ are independently hydrogen optionally substituted alkyl, optionally substituted cycloalkyl, optionally substituted aryl.

Another preferred embodiment of the invention is a hydroperoxide having formula D, wherein $R_4$, $R_6$, $R_7$, $R_{10}$, and $R_{11}$ are independently hydrogen, optionally substituted alkyl, optionally substituted cycloalkyl, optionally substituted aryl, $R_{12}CO$, $COOR_{13}$, $OR_{14}$, and $NR_{15}R_{16}$, and $R_1$, $R_2$, $R_3$, $R_5$, $R_8$, $R_9$, $R_{12}$, $R_{13}$, $R_{14}$, $R_{15}$, and $R_{16}$ are independently hydrogen, optionally substituted alkyl, optionally substituted cycloalkyl, optionally substituted aryl. The hydroperoxide of formula D comprises at least two chiral centers at C3 and C7, and thus, has two pairs of enantiomers having the absolute configuration of (S, S), (R, R), (R, S), and (S, R). The compound may be enatiomerically pure or a mixture of two or more of the stereoisomers.

In a more preferred embodiment, the hydroperoxide compound has the structure formula of D, wherein $R_4$, $R_5$, $R_{10}$, and $R_{11}$ are independently optionally substituted alkyl, and $R_1$, $R_2$, $R_3$, $R_6$, $R_7$, $R_8$, and $R_9$ are independently hydrogens.

In another preferred embodiment, the epoxide of formula A or B, or the hydroperoxide of formula C or D has antifungal activity against pathogenic mammalian fungi, more preferably against human pathogenic fungi. There are over 300 known human pathogenic fungi, including but not limited to, *Microsporum canis*, *Microsporum gallinna*, *Candida albican*, *Candida auris*, *Aspergillus fumigtus*, *Asper-*

*gillus flavus, Cryptococcus neoformans, Cryptococcus gattii, Histoplasma capsulatum*, and *Stachybotrys chartarum*.

A second aspect of the invention is directed to a method of making an epoxide of formula A or B, or hydroperoxide of C or D from a compound having formula E, wherein $R_4$, $R_6$, $R_7$, $R_8$, and $R_9$ are independently hydrogen, optionally substituted alkyl, optionally substituted cycloalkyl, optionally substituted aryl, $R_{13}CO$, $COOR_{14}$, $OR_{15}$, and $NR_{16}R_{17}$, and $R_1$, $R_2$, $R_3$, $R_5$, $R_{10}$, $R_{11}$, $R_{12}$, $R_{13}$ $R_{14}$, $R_{15}$, $R_{16}$, and $R_{17}$ are independently hydrogen, optionally substituted alkyl, optionally substituted cycloalkyl, optionally substituted aryl.

Formula E

A preferred embodiment the method utilized a compound of formula E, wherein $R_4$, $R_5$, $R_{11}$, and $R_{12}$ are optionally substituted alkyl, optionally substituted cycloalkyl, optionally substituted aryl, and $R_1$, $R_2$, $R_3$, $R_5$, $R_6$, $R_7$, $R_8$, $R_9$, and $R_{10}$ are independently hydrogen.

Figure 2:
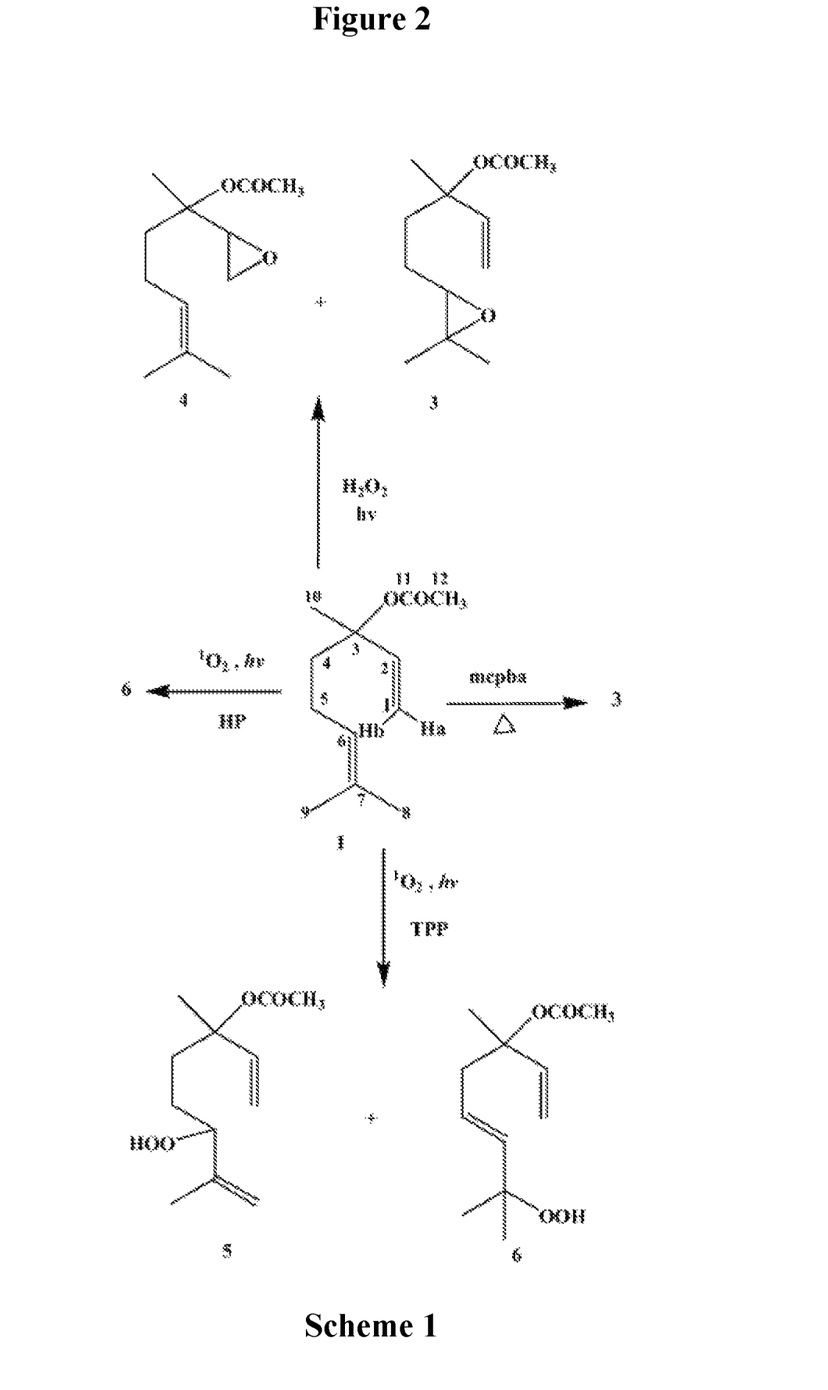
FIG. 2 shows the products of photo and thermal epoxidation, and photooxygenation of linalyl acetate (Scheme 1).

A preferred embodiment of the method is a photochemical method comprises irradiating a solution of compound formula E in a solvent in the presence of hydrogen peroxide to produce a mixture of compounds 3 and 4 (see Scheme 1 in FIG. 2). Any source of light may be used in the irradiation including, but not limited to, sodium lamp and sun light, preferably sodium lamp. Similarly, the solvent may be any solvent miscible with aqueous solution of hydrogen peroxide, such as but not limited to, methanol, ethanol, propanol, isopropanol, butanol, and isobutanol. In a preferred embodiment of the method, the solvent is selected from the group consisting of methanol, ethanol, propanol, and isopropanol. In a more preferred embodiment, the alcohol is ethanol.

In a more preferred embodiment, the method utilizes a compound of formula E, wherein $R_4$, $R_6$, $R_7$, $R_8$, and $R_9$ are independently hydrogen, optionally substituted alkyl, optionally substituted cycloalkyl, optionally substituted aryl, and $R_1$, $R_2$, $R_3$, $R_6$, $R_7$, $R_8$, $R_9$, and $R_{10}$ are independently hydrogen, optionally substituted alkyl, optionally substituted cycloalkyl, optionally substituted aryl.

In another preferred embodiment of the method, the solution contains hydrogen peroxide at concentration in the range of 1.0% to 15% (v/v), more preferably in the range of 2% to 10% (v/v), even more preferably in the range of 3% to 8% (v/v), and most preferably in the range of 4% to 6% (v/v). In a particularly preferred embodiment, the solution contained about 4% hydrogen peroxide. The method produces the epoxide 3 and 4 from the compound 1. The two products may be separated by any method known in the art such as, but not limited to, fractional crystallization and chromatography.

In an embodiment, the product of the method is enantiomerically pure. If the starting material of the method is a single enantiomer (S) or (R), the resulting product is a mixture of pair of diasteromers (S, S) and (S, R) or (R, S) and (R, R), respectively. Diastereomeric compounds may be separated by any chromatographic method known in the art or fractional distillation or crystallization. On the other hand, if a racemic mixture of formula E is used as a starting material, two pairs of diastereomeric compounds are produced which can be separated to two racemic mixtures of the resulting epoxide. Resolution of enantiomeric pairs is well-known in the art such as, but not limited to, chromatography on chiral support.

Another preferred embodiment is a photochemical method of producing a hydroperoxides of formula C or D. The method comprises irradiating a solution of compound of formula E in a solvent in the presence of oxygen and a photosensitizer. Any suitable source of light may be used to irradiate the solution including, but not limited to, sodium lamp and sun light, preferably sodium lamp. Similarly, the solvent may be any solvent such as but not limited to chloroform, methylene chloride, tetrachlormethane, hexane, pentane, methanol, ethanol, propanol, isopropanol, butanol, and isobutanol. In a preferred embodiment of the method, the solvent is selected from the group consisting of chloroform, methylene chloride, tetrachlormethane, hexane, and pentane. In a more preferred embodiment, the solvent is chloroform. There are many photosensitizers known in the art including, but not limited to, dyes such as rose Bengal, methylene blue, and porphyrin derivatives such as tetraphenylporphorin (TPP) and hematoporphorin (HP). It should be noted that hydroperoxide compounds may be obtained by well-known methods in the art from an alcohol precursor by oxidation with sulfuric acid or perchlorate salt such as sodium or potassium perchlorate.

In a more preferred embodiment, the method comprising irradiating a solution of compound 1 in chloroform in the presence of the photosensitizer TPP to produce the hydroperoxide 5 and 6. The method may include purification of compounds 5 and 6. The purification method may include chromatographic step on silica column or fractional distillation.

In another preferred embodiment of the method, the photosensitizer HP is used to produce compound of formula D.

In a more preferred embodiment of the method, compound 1 is irradiated in the presence of HP to produce only compound 6.

Other epoxidation methods to obtain the epoxides of the invention are well-known in the art including but limited to the use m-chlorperbenzoic acid and t-butylperoxide. For example, the reaction of compound 1 with m-chlorperbenzoic acid in chloroform produces compound 3 only. In contrast, the Sharpless epoxidation method [Katsuki and Sharpless (1980) J. Am. Chem Soc, 102, 5974-5976] is both regioselective and enantioselective method and suitable to produce all four stereoisomers of compound 4. The method is utilized to obtain chiral epoxides from allylic alcohol. For example, an entiomerically pure compound 2 (see Scheme 1) can be epoxidized with t-butylperoxide in the presence of (−) or (+)-diethyltartarate and titanium tetra(isopropoxide) to produce a chiral epoxide, which can be acylated by well-known methods in the art to produce a chiral compound 4. The only expected epoxide formed by the method from compound 2 results from the epoxidation of the C1-C2 double bond only.

Pharmaceutical Composition:

A third aspect of the invention is related to a pharmaceutical composition comprising one or more compounds of formula A.

As used herein, a "composition" or a "pharmaceutical composition" refers to a mixture of the active ingredient with other chemical components, such as pharmaceutically acceptable carriers and excipients. One purpose of a composition is to facilitate administration of the epoxides and/or hydroperoxides of the invention. Pharmaceutical compositions of the present disclosure may be manufactured by processes well-known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, one or more compound having a structure selected from the group consisting of formula A, formula B, formula C, and formula D.

In a preferred embodiment, the active ingredient selected from compound 1, 3, 4, 5, 6, and stereoisomers thereof.

A preferred embodiment, the pharmaceutical composition comprises one or more of the compounds of the invention in the range of 0.1% to 20%, more preferably in the range of 0.5% to 10%, even more preferably in the range of 1.0% to 5%, and most preferably 2% to 4% based on the total weight of the composition.

In some embodiments, the pharmaceutical composition comprises up to 0.1 wt. %, 1 wt. %, 5 wt. %, or 10 wt. % of a pharmaceutically acceptable salt. In some embodiments, the pharmaceutical composition comprises up to 0.1 wt. %, 0.5 wt. %, 1.0 wt. %, 2.0 wt. %, 3.0 wt. %, 4.0 wt. %, 5.0 wt. %, or 10.0 wt. % of a pharmaceutically acceptable solvate. Preferably, the pharmaceutical composition may further comprise pharmaceutically acceptable binders, such as sucrose, lactose, glucose, fructose, galactose, mannitol, xylitol, and pharmaceutically acceptable excipients such as calcium carbonate and calcium phosphate.

In some embodiments, the ability of the active ingredient to reduce and limit the infectivity of a fungus may be tested by the well-cut diffusion method described herein (see example 1).

In a preferred embodiment, the pharmaceutical composition comprises in the range of 1.0 mM to 20 mM, preferably in the range of 2 mM to 15 mM, more preferably, 3 mM to 10 mM, and most preferably 4 mM to 8 mM of the antifungal compounds relative to the total volume of the composition.

In another preferred embodiment, the pharmaceutical composition comprises one or more carriers and/or excipients selected from the group consisting of a buffer, an inorganic salt, a fatty acid, a vegetable oil, a synthetic fatty ester, a surfactant, a sugar, a polymer, and combination thereof.

In another preferred embodiment, the pharmaceutical composition may comprise other active ingredients in addition to antifungal compounds of the invention. In one embodiment, the other active ingredient may be an antiviral agent, for the treatment or prevention of secondary infection in the subject. Antiviral drugs include, but not limited to, ketoconazole, fluconazole, isavuconazole, itraconazole, posaconazole, posaconazole, voriconazole, anidulafungin, caspofungin, micafungin and the like.

In another preferred embodiment, the other active ingredient may be antibiotic compounds such as, but not limited to Vancomycin, Ceftobiprole, Ceftaroline, Clindamycin, Dalbavancin, Daptomycin, Fusidic acid, Linezolid, Mupirocin, Oritavancin, Tedizolid, Telavancin, Tigecyclin, Aminoglycosides, Carbapenems, Ceftazidime, Cefepime, Ceftobiprole, Ceftolozane/tazobactam, Fluoroquinolones, Piperacillin/tazobactam, Ticarcillin/clavulanic acid, Linezolid, Streptogramins, Tigecycline, and Daptomycin As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it contains. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include antioxidants including ascorbic acid; low molecular weight (less than about 10 residues) peptides; proteins, such as serum albumin, gelatine, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrin; chelating agents such as EDTA; sugar alcohols such as mannitol or sorbitol; salt-forming counter ions such as sodium; and/or non-ionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatine, vegetable oils, and polyethylene glycols.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate/bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)-dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethyl-ammonium bromide, tetradecyltrimethylammonium bromide, tetradecyltrimethylammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphos-phazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatine, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethylacetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the composition comprising the antiviral peptides disclosed herein has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about one hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least one hour following oral administration. In another embodiment, controlled-release results in substantially complete dissolution after at least one hour following rectal administration. In one embodiment, the composition is not a controlled-release composition.

Methods of Treatment and Protecting a Subject from Fungal Infection

A fourth aspect of the invention is directed to a method of treatment of a subject suffering from fungal infection, or protecting a subject from getting infected with a fungus. The method comprises administering to a subject infected with fungus an effective amount of the pharmaceutical composition described here. Treatment is preferably commenced at the time of infection or post infection with fungus. It is recommended that the treatment continues until the fungus is no longer present or active as demonstrated by the disappearance of any symptoms related to the infection. For protecting a subject from infection, the treatment continues for as long as there is a potential exposure to the fungal source.

The amount of the pharmaceutical composition administered to a subject varies and it is dependent on the age and weight of the subject as well as the severity of the infection. Suitable treatment is given 1-4 times daily and continued for 3-10 days, and typically 8 days post infection. In some instances, the treatment may continue for a longer period of time at a lower dosage to insure that the fungal infection has been completely treated. The desired dose may be presented in a single dose or as divided doses administered at appropriate intervals, for example as two, three, four or more sub-doses per day. The pharmaceutical composition may be conveniently administered in unit dosage form, wherein the peptide content of the pharmaceutical composition is in the range of 10 to 1500 mg, conveniently 20 to 1000 mg, most conveniently 50 to 700 mg of active ingredient per unit dosage. Usually, the dose of the compound is in the range of 1 mg/kg to 150 mg/kg of body weight, preferably in the range of 25 mg/kg to 100 mg/kg of body weight, more preferably in the range of 50 mg/kg to 90 mg/kg of body weight, and most preferably in the range of 70 mg/kg to 80 mg/kg of body weight.

In some other embodiment, the method of treatment may be accompanied by other modes of treatment of fungal infection such as, but not limited to, laser treatment or UV exposure.

The examples below are intended to further illustrate protocols for the preparation and characteristics of the epoxides and hydroperoxide described above, and are not intended to limit the scope of the claims.

Example 1

Materials and Methods
Chemistry:

Linalyl acetate was extracted from lavender essential oil. Lavender was collected from Albaha City, Kingdom of Saudi Arabia. IR spectra were performed on a NICOLET IS50 FT-IR spectrophotometer. $^1$H NMR spectra was obtained in $CDCl_3$ solution with a Brucker Ascend TM 850 MHz apparatus. A Philips G/5812 SON sodium lamp was used as irradiation source in photo-initiated reactions. Thin layer chromatography (TLC) and preparative layer chromatography [(PLC): Polygram SIL G/W 254 silica gel, Mecherey-Nagel. A rotatory evaporator (at 20° C./15 torr) was used to remove the solvents.

Antimicrobial Activity

Fungi:

*Microsporum canis* and *Microsporum gallinna* were obtained from King Fahad Hospital in Jeddah, Saudi Arabia Antifungal Activity by the Well-Cut Diffusion Method:

Well-cut diffusion technique was used to evaluate the antifungal activities of the tested compounds [El-Masry et al. "Synthesis and antimicrobial activity of some new benzimidazole derivatives" Molecules, 5 (2002), pp. 1429-1438]. The Sabaroud dexterous agar media was inoculated with 1 ml from tested spore suspension, then wells were cut from the plate using a sterile 10 mm cork-borer. About 0.5 and 1.0 ml of a chloroform solution containing 1.0 mg/ml of tested compounds were added into each well. All plates were incubated at 4° C. for 2 h to slow fungal growth. The plates were later incubated at 28° C. for a week [Mtolera and Semesi "Antimicrobial activity of extracts from six green algae from Tanzania." Curr. Trends Mar. Bot. Res. East Afr. Reg. pp. 211-217 (1996)]. After incubation, the diameter of the growth inhibition zone was measured in mm [Attaie et al. Inhibition of growth of *S. aureus* during production of acidophilus yogurt J. Food Prot., 50 (1987), pp. 224-228], see Table 3.

Example 2

Epoxidation Procedures of 1:

Method A: Photochemical Epoxidations Photochemically by Hydrogen Peroxide:

A solution of $H_2O_2$ (2.5 ml, 50%) was added drop wise over 5 min to a stirred solution of 1 (5 mmol) in ethanol (25 ml) at 0° C. The mixtures were irradiated using sodium lamp in an atmosphere of nitrogen for 15 hours. The reaction mixture was evaporated under reduced pressure at room temperature which was purified by column chromatography on silica gel eluted with a mixture of petroleum ether (bp 60-80° C.) and ethyl acetate (8:2) [Elgendy and Khayyat, 2008a, 2008b] to give a mixture of 3 and 4. The results were given in Table 1.

TABLE 1

Thermal and Photochemical epoxidation of linalyl acetate.

| Compound No. | Start wt. g | Epoxidation method | Solvent | Yield | Epoxidation Product Compound | % |
|---|---|---|---|---|---|---|
| 1 | 2 | Thermal (mcpba) | $CHCl_3$ | 83% | 3 | 80 |
| 1 | 2 | Photochemicall $(H_2O_2)$ | $C_2H_5OH$ | 75% | 3 | 50 |
|   |   |   |   |   | 4 | 20 |

Method B: Thermal Epoxidations Using m-Chloroperbenzoic Acid:

A solution of m-chloroperbenzoic acid (mcpba, 10 mmol dissolved in chloroform) was added cautiously drop wise over 15 min to a stirred solution of 1 (5 mmol) in chloroform (25 ml) at 0° C. The mixture was continued to be stirred under nitrogen at room temperature, and the reaction is monitored by TLC on silica-gel plates visualized by peroxide test by KI, 10% in water. The chloroform solution was carefully washed with a saturated aqueous solution of $NaHCO_3$ (3×10 ml), and with distilled water (3×10 ml). The organic layer was separated, dried over anhydrous $Na_2SO_4$, and evaporated under reduced pressure at room temperature [Khayyat, S. "Epoxidation of curcumin belongs to curcuminoids" Adv. Sci. Lett., 5 (2012), pp. 387-391]. The crude residue product was purified by column chromatography on silica gel adsorbent. Elution of the column with solvent mixture of petroleum ether 60-80° C. and ether (9:2) gave the epoxide derivatives (Table 1).

Example 3

Photooxygenation of 1

A solution of compound 1 (10 mmol) of linalyl acetate in chloroform, according to the type of sensitizers, was irradiated externally by means of sodium lamp at −5° C. During the irradiation, a continuous stream of dry oxygen gas was allowed to pass through the reaction mixtures at a slow rate to avoid evaporation of solvent. The solvent was evaporated at 20° C./15 Torr. The crude products were purified by column chromatography on silica gel adsorbent by eluting with a mixture of petroleum ether 60-80° C. and ethyl acetate (8:2) [Khayyat, S. "Photosynthesis of Safrole types potential intercalative and oxidative agent of DN through photooxidation reaction" Aust. J. Bas. App. Sci., 5 (5) (2011), pp. 78-81; and; Khayyat and Al-Zahrani "Thermal, photosynthesis and antibacterial studies of bioactive safrole derivative as precursor for natural flavor and fragrance" Arab. J. Chem., 7 (2014), pp. 800-804]. The solvents, sensitizers, reaction time, the yields and photo-products were given in Table 2.

TABLE 2

Photosensitized oxygenation of linalyl acetate in the presence of hematoporphrin (HP) tetraphenylporphyrin (TPP).

| Comp. No. | Starting Wt. g | Sensitizer | Solvent | Irradiation time | Yield | Photo products Compound | % |
|---|---|---|---|---|---|---|---|
| 1 | 1 | TPP | $CHCl_3$ | 12 | 70% | 5 | 30 |
|   |   |   |   |   |   | 6 | 32 |
| 1 | 1 | HP | $CHCL_3$ | 12 | 55% | 6 | 50 |

Example 4

Spectroscopic Data 3,7-Dimethyl-1,6-octadien-3-yl acetate (1)

Colorless liquid, $C_{12}H_{20}O_2$ (M. wt. 196.29). IR (thin film): $v^{-1}$: 3460, 2973, 2879, 1720, 1736, 1367, 1237, 1110 cm$^{-1}$. $^1$H NMR (CDCl$_3$) δ ppm: 1.35 (s, 3H, $^{10}CH_3$), 1.40 (s, 3H, $^9CH_3$), 1.48 (s, 3H, $^8CH_3$), 1.62 (comp. pat., 2H, H-4), 1.79 (comp. pat., 1H, H-5), 1.94 (s. s, 3H, $^{12}CH_3$), 4.92 (t, 1H, H-6), 4.95 (dd, 1H, J=7.2, H-1), 4.97 (dd, 1H, J=11.1, H-1), 5.79 (dd, 1H, J=11.6, H-2). $^{13}$C NMR spectrum, δ ppm: 17.1 (C12), 21.3 (C5), 21.9 (C8), 23.1 (C10), 25.1 (C9), 39.9 (C4), 81.8 (C3) 111.2 (C1), 122.3 (C6), 133.2 (C7), 141.1 (C2), 169.5 (C11).

6,7-Epoxy-3,7-dimethyl-1-octene-3-yl-acetate (3)

Colorless liquid, $C_{12}H_{20}O_3$ (M. wt. 212.29). IR (thin film): $v^{-1}$: 3627, 3089, 2979, 2880, 1735, 1451, 1367, 1237, 1118 cm$^{-1}$. $^1$H NMR (CDCl$_3$) δ ppm: 1.18 (s, 3H, $^9CH_3$), 1.22 (s, 3H, $^8CH_3$), 1.47 (d, 2H, H-5), 1.52 (comp. pat., 2H, H-4), 1.60 (s, 3H, $^{10}CH_3$), 1.94 (s. s, 3H, $^{12}CH_3$), 2.61 (comp. pat., 1H, H-6), 5.04 (dd, 1H, J=7.1, H-1), 5.08 (dd, 1H, J=11.0, H-1), 5.79 (dd, 1H, J=11.6, H-2). $^{13}$C NMR spectrum, δ ppm: 17.4 (C12), 18.4 (C5), 21.9 (C8), 22.1 (C9), 23.1 (C10), 36.1 (C4), 57.5 (C7) 63.7 (C6), 77.2 (C3), 114 (C1), 141.1 (C2), 169.5 (C11).

1,2-Epoxy-3,7-dimethyl-6-octene-3-yl acetate (4)

Colorless liquid, $C_{12}H_{20}O_3$ (M. wt. 212.29). IR (thin film): $v^{-1}$: 3630, 3088, 2980, 2879, 1758, 1455, 1371, 1119 cm$^{-1}$. $^1$H NMR (CDCl$_3$) δ ppm: 1.51 (s, 3H, $^{10}CH_3$), 1.60 (t, 2H, H-4), 1.75 (s, 3H, $^8CH_3$), 1.80 (s, 3H, $^9CH_3$), 2.00 (comp. pat., 1H, H-5), 2.05 (s, 3H, $^{12}CH_3$), 2.70 (comp. pat., 2H, H-1), 3.1 (comp pat., 1H, H-2), 5.45 (comp. pat., 1H, H-6). $^{13}$C NMR spectrum, δ ppm: 17.5 (C5), 18.0 (C12), 19.4 (C9), 20.6 (C10), 25.4 (C8), 36.6 (C4), 39.5 (C1) 63.6 (C2), 78.9 (C3), 126.2 (C6), 133.3 (C7), 171.2 (C11).

6-Hydroperoxy-3,7-dimethylocta-1,7-diene-3-yl acetate (5)

Colorless liquid, $C_{12}H_{20}O_4$ (M. wt. 228.14). IR (thin film): $v^{-1}$: 3397, 3089, 2980, 2252, 1716, 1368, 1240, 1019 cm$^{-1}$. $^1$H NMR (CDCl$_3$) δ ppm: 1.32 (s, 3H, $^{10}CH_3$), 1.53 (t, 2H, H-5), 1.72 (s, 3H, $^9CH_3$), 2.0 (d, 2H, H-4), 2.17 (s, 3H, $^{12}CH_3$), 4.28 (t, 1H, H-6), 5.14 (comp. pat., 1H, H-8), 5.62 (comp. pat, 2H, H-1), 5.98 (q, 1H, H-2), 7.97 (s, 1H, OOH). $^{13}$C NMR spectrum, δ ppm: 17.1 (C9), 22.1 (C12), 23.4 (C10), 24.3 (C5), 35.6 (C4), 77.1 (C3), 89.3 (C6) 113.5 (C8), 137.5 (C2), 141.4 (C1), 143.2 (C7), 170.0 (C11).

7-Hydroperoxy-3,7-dimethylocta-1,5-diene-3-yl acetate (6)

Colorless liquid, $C_{12}H_{20}O_4$ (M. wt. 228.14). IR (thin film): $v^{-1}$: 3401, 2978, 2753, 1732, 1239, 1368, 1019 cm$^{-1}$. $^1$H NMR (CDCl$_3$) δ ppm: 1.33 (s, 3H, $^9CH_3$), 1.50 (s, 3H, $^8CH_3$), 1.97 (s, 3H, $^{10}CH_3$), 2.2 (s, 3H, $^{12}CH_3$), 2.57 (d, 2H, H-4), 5.12 (comp. pat, 2H, H-1), 5.60 (t, 1H, H-6), 5.89 (comp. pat, 1H, H-5), 5.95 (comp. pat, 1H, H-2), 7.8 (s, 1H, OOH) ppm. $^{13}$C NMR spectrum, δ ppm: 17.6 (C12), 22.2 (C9), 22.34 (C8), 23.6 (C10), 42.2 (C4), 76.9 (C7), 77.3 (C3) 113.5 (C6), 123.8 (C5), 133.3 (C1), 142.9 (C2), 170.1 (C11).

Linalyl acetae [3,7-Dimethylocta-1,6-dien-3-yl acetate] (1) is one of the major components of lavender essential oil which can be easily extracted by steam distillation from *Lavandula* [Koulivand et al. Lavender and the nervous system Evid.-Based Complement. Altern. Med., 2013 (2013), pp. 10-20; Prusinowska, and Krzysztof "Composition, biological properties and therapeutic effects of lavender (*Lavandula angustifolia* L.)" A review. Herba Bonica 60(2), 56-66]. The chemical structure of 1 was confirmed by spectral measurements. $^1$H NMR spectrum of 1 showed doublet of doublet at δ 4.95 ppm and 4.97 ppm of protons of C1, and doublet of doublet at δ 5.79 ppm of protons of C2. The $^{13}$C NMR spectrum of 1 shows that C1 and C2 signals observed at δC 111.2 and 141.1 ppm, respectively. The signal at δC 169.5 ppm is assigned to C11 carbonyl group. Thermal epoxidation of linalyl acetate (1) using mcpba in chloroform gave 80% linalyl epoxide (3) (Scheme 1). On the other hand, photochemical epoxidation of 1 with hydrogen peroxide ($H_2O_2$, 30% by volume) in ethanol under irradiation with sodium light (irradiation time 15 h) gave 50% of 6,7-epoxy-3,7-dimethyl-1-octene-3-yl acetate (3) and 18% of 1,2-epoxy-3,7-dimethyl-6-octene-3-yl acetate (4) (Scheme 1). The structures of epoxidation products 3 and 4 were established by spectral measurements. IR spectrum of 3 had an absorption band similar to that observed for 4. $^1$H NMR spectrum of 3 showed doublet of doublet at δ 5.04 and δ 5.08 from protons Ha-1 and Hb-1, respectively. The other proton spectra has complex pattern at δ 2.61 ppm from H-6 in the oxiran ring. Compound 4 displayed in the $^1$H NMR spectrum two complex pattern at δ 2.7 ppm and δ 3.1 ppm for two protons of H-1 and one proton of H-2 in the oxirane ring, respectively. $^{13}$C NMR spectrum of 3 showed signals of the oxirane carbon atoms at δ 57.5 (C7) and δ 63.7 ppm (C6). In contrast, compound 4 showed signals at δ 39.5 (C1) and δ 63.5 ppm (C2) of oxiran carbon atoms.

The photooxygenation reaction of 1, in the presence of tetraphenyl porphin (TPP) as singlet oxygen sensitizers gave a mixture of 6-hydroperoxy-3,7-dimethylocta-1,7-diene-3-yl acetate (compound 5) and 7-hydroperoxy-3,7-dimethyl-octa-1,5-diene-3-yl-acetate (compound 6). However, compound 6 was obtained only by using hematoporphyrin (HP) as sensitizer. Fortunately, hydroperoxide 5 and 6 can be separated (Scheme 1).

The structures of compounds 5 and 6 were supported by spectral studies. IR spectrum of 5 had similar absorption band as those observed for 6. $^1$H NMR spectrum of 5 showed complex pattern at δ 5.14 ppm for H-8 and singlet at δ 7.97 ppm for OOH group, whereas the $^1$H NMR spectrum of 6 showed tertiary signal at δ 5.60 ppm for H-6 and complex pattern at δ 5.89 ppm for H-5 and singlet at δ 7.8 ppm for OOH group. $^{13}$C NMR spectrum of 5 showed signals of the ethylene carbon atoms at δ 113.5 and δ 143.2 for (C8 and C7), respectively, whereas compound 6 showed signals at δ 113.5 for (C6) and signal at δ 123.8 for (C5).

The epoxidation of linalyl acetate (compound 1) with m-chloroperbenzoic acid thermally gave compound 3. However, the photo-epoxidation of 1 using hydrogen peroxide in ethanol solution gave a mixture of compounds 3 and 4 in the ratio of 5:2, respectively (Scheme 1).

Figure 3:
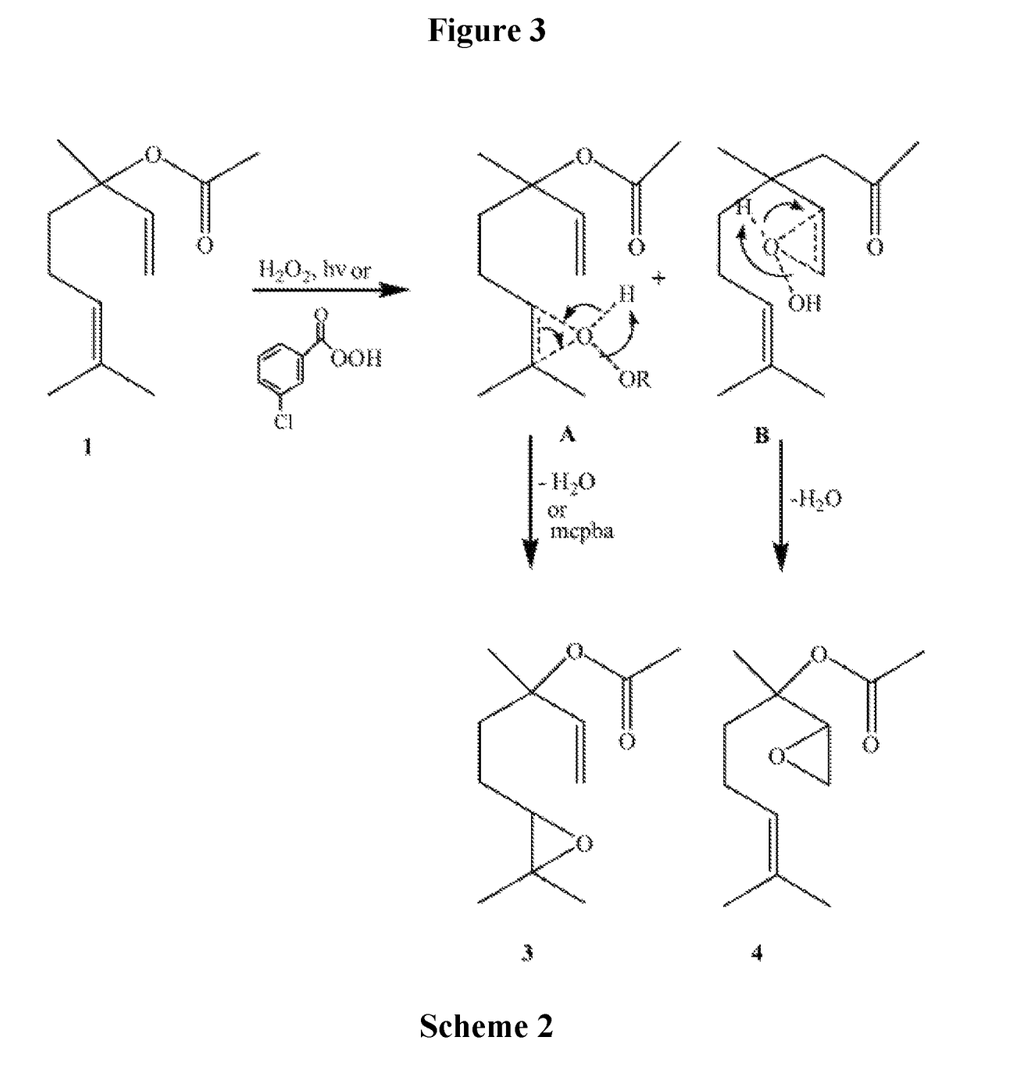
FIG. 3 shows the mechanism of thermal and photochemical epoxidation of linalyl acetate (Scheme 2).

The probable mechanism for production of epoxide compound 3 and 4 is believed to be through the formation of the oxirane intermediates A and B via elimination of $H_2O$ or m-chlorobenzoic acid [depending on the epoxidizing agents, which were used $H_2O_2$ or mcpba] (Scheme 2).

On the other hand, our interest was focused on the photooxygenation reaction of linalyl acetae 1 using different singlet oxygen sensitizers which gave a mixture of (6-hydroperoxy-3,7-dimethyl-octa-1,7-diene-3-yl-acetate (compound 5) and 7-hydroperoxy-3,7-di-methyl-octa-1,5-diene-3-yl acetate (compound 6) using TPP while HP gave only compound 6 (Scheme 1).

Figure 4:
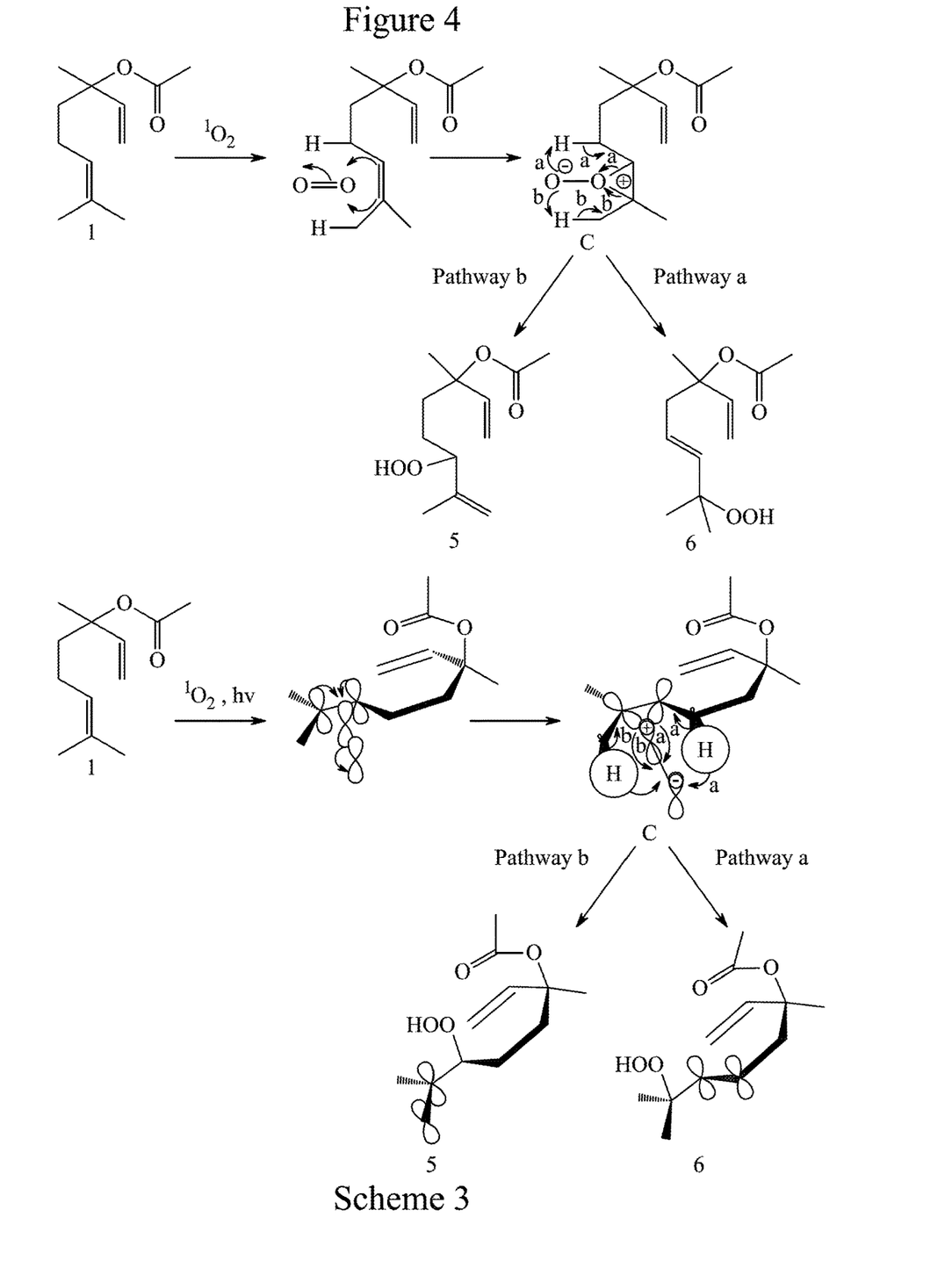
FIG. 4 shows the mechanism of photooxygenation of linalyl acetate (Scheme 3).

The formation of hydroperoxides of compounds 5 and 6 may be assumed to proceed via peroxirane transition state (C), which has been done through two probable pathways (see Scheme 3).

Example 5

Antimicrobial Activity

In recent years, essential oils have been reported to be a good source of antifungal and antibacterial compounds [Nor Azah et al. "Chemical composition and antimicrobial activities of the essential oils of *Cinnamomum aureofulvum*" GambEssent Oil Res., 14 (2002), pp. 135-138; Tabassum and Vidyasagar "Antifungal investigations on plant essential oils. A review" Int. J. Pharm Pharm. Sci, 5 (2) (2002), pp. 19-28]. Many monoterpenes were shown to act effectively in chemoprevention and chemotherapy. Also, the compounds were proved to be active against many pathogenic bacteria [Saddiq and Khayyat "Chemical and antimicrobial studies of monoterpene: citral Pest". Biochem. Physiol., 98 (2010), pp. 89-91].

A comparative study of the antifungal activities of compound 1 and 3-6 was carried out against the human pathogen fungal species *Microsporum canis* and *Microsporum gallinna*. The fungal species are a part of a group of fungi known as communicable pathogen dermatophytes [Michiko et al. "Isolation of *Microsporum gallinae* from a fighting cock (*Gallus gallus domesticus*) in Japan" Med. Mycol., 51 (2) (2013), pp. 144-149; and Shafiee et al. "Comparative study of *Microsporum canis* isolates by DNA fingerprinting" Mycoses, 57 (2014), pp. 507-512]. The results clearly indicated that linalyl acetate 1, epoxides 3 and 4, and hydroperoxides 5 and 6, strongly inhibited *Microsporum canis* and *Microsporum gallinna* grown on the solid media, see Table 3. It showed that all linalyl acetate and its derivatives were effective in reducing the growth of tested fungi. All the tested compounds inhibited *M. canis* and *M. gallinna* growth completely at concentration of 1 mg/ml except in the case of epoxide 3 on *M. canis*. Hydroperoxide 5 was displayed the highest antimicrobial activity at 0.5 mg/ml concentration against *M. canis* and *M. gallinna* (Table 3). The results indicated that compounds are beneficial to human health, and have the potential to be used for medicinal purposes.

TABLE 3

Inhibition activity of the tested epoxides 3 and 4, and hydroperoxides 5 and 6_against *Microsprum gallinna* and *Microsporum canis*.

| Type of extract | Concentration mg/mL | Inhibition Zone Dimeter (mm) | |
|---|---|---|---|
| | | M. gallina | M. canis |
| Control | 0.0 | — | — |
| Linalyl acetate | 0.5 | 80.0 | 80.0 |
| | 1.0 | 85.0 | 85.0 |
| Epoxide 3 | 0.5 | 37.0 | 60.0 |
| | 1.0 | 74.0 | 85.0 |
| Epoxide 4 | 0.5 | 65.0 | 75.0 |
| | 1.0 | 85.0 | 85.0 |
| Hydroperoxide 5 | 0.5 | 80.5 | 81.0 |
| | 1.0 | 85.0 | 85.0 |
| Hydroperoxide 6 | 0.5 | 80.0 | 80.0 |
| | 1.0 | 85.0 | 85.0 |

The results of disclosure demonstrated the antifungal activities linalyl acetate and its epoxide and hydroperoxide derivatives. The results proved that epoxides and hydroperoxides of linalyl acetate can be formulated into effective drugs for the treatment and preventing fungal infection in mammals including humans.

The invention claimed is:

1. A pharmaceutical composition, comprising:
   two epoxide compounds, and
   at least one adjuvant and/or excipient selected from the group consisting of benzyl alcohol, propylene glycol, polyethylene glycol, a vegetable oil, a fatty acid, a synthetic fatty ester, a surfactant, and a sugar,
   wherein the epoxide compounds consist of the compounds of formula 3 and 4:

Formula 3

Formula 4 wherein each of the compounds of formula 3 and 4 are present in the pharmaceutical composition in an equal amount in the range of 0.1%-20% by weight of the total weight of the pharmaceutical composition.

2. The pharmaceutical composition of claim 1 further comprising:
   at least one compound selected from the group consisting of linalyl acetate, the hydroperoxide compound of formula 5, and the hydroperoxide compound of formula 6:

Formula 5

Formula 6 wherein the compound is present in the pharmaceutical composition in an amount in the range of 0.1-20% by weight of the total weight of the pharmaceutical composition.

3. The pharmaceutical composition of claim 1, further comprising:
   water and/or a buffer.

4. The pharmaceutical composition of claim 3, wherein the buffer is selected from the group consisting of a phosphate buffer, a citrate buffer, an acetate buffer, a borate buffer, and a carbonate/bicarbonate buffer.

5. The pharmaceutical composition of claim 1, further comprising:
   one or more antiviral drugs.

6. The pharmaceutical composition of claim 5, wherein the antiviral drug is one or more antiviral agents selected from the group consisting of ketoconazole, fluconazole, isavuconazole, itraconazole, posaconazole, posaconazole, voriconazole, anidulafungin, caspofungin, and micafungin.

7. The pharmaceutical composition of claim 1, further comprising:
   one or more antibiotic compounds.

8. The pharmaceutical composition of claim 7, wherein the antibiotic compound is one or more antibiotics selected from the group consisting of Vancomycin, Ceftobiprole, Ceftaroline, Clindamycin, Dalbavancin, Daptomycin, Fusidic acid, Linezolid, Mupirocin, Oritavancin, Tedizolid, Telavancin, Tigecyclin, Aminoglycosides, Carbapenems, Ceftazidime, Cefepime, Ceftobiprole, Ceftolozane/tazobactam, a fluoroquinolone, Piperacillin/tazobactam, Ticarcillin/clavulanic acid, Linezolid, Streptogramins, Tigecycline, and Daptomycin.

9. The pharmaceutical composition of claim 1 which is formulated for immediate release.

10. The pharmaceutical composition of claim 1 which is formulated for controlled release.

11. The pharmaceutical composition of claim 1 which is formulated as a solid for oral administration.

12. The pharmaceutical composition of claim 1 which is formulated as a liquid for oral administration.

13. The pharmaceutical composition of claim 1 which is formulated as a liquid for parenteral administration.

14. The pharmaceutical composition of claim 1 which is formulated for topical administration.

15. A method of treating a subject having a *Microsporum gallinna* and *Microsporum canis* fungal infection, comprising:
    administering to the subject an antifungal effective amount of the pharmaceutical composition of claim 1.

16. A method of treating a subject having a *Microsporum gallinna* and *Microsporum canis* fungal infection, comprising:
    administering to the subject an antifungal effective amount of the pharmaceutical composition of claim 2.

17. The method of claim 15, wherein the subject is a mammal.

18. The method of claim 15, wherein the subject is a human.

* * * * *